(12) United States Patent
Boyd et al.

(10) Patent No.: US 8,940,766 B2
(45) Date of Patent: Jan. 27, 2015

(54) METHODS FOR PREVENTING AND/OR TREATING LYSOSOMAL STORAGE DISORDERS

(75) Inventors: Robert Boyd, Horsham, PA (US); Gary Lee, West Windsor, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 773 days.

(21) Appl. No.: 12/757,160

(22) Filed: Apr. 9, 2010

(65) Prior Publication Data

US 2010/0260740 A1    Oct. 14, 2010

Related U.S. Application Data

(60) Provisional application No. 61/168,109, filed on Apr. 9, 2009.

(51) Int. Cl.
| | | |
|---|---|---|
| *A61K 31/445* | (2006.01) | |
| *C07D 211/36* | (2006.01) | |
| *C07D 211/44* | (2006.01) | |
| *C12Q 1/34* | (2006.01) | |

(52) U.S. Cl.
CPC ............... *C12Q 1/34* (2013.01); *C07D 211/36* (2013.01); *A61K 31/445* (2013.01); *G01N 2333/924* (2013.01)
USPC .......................................... 514/315; 546/242

(58) Field of Classification Search
None
See application file for complete search history.

(56) References Cited

U.S. PATENT DOCUMENTS

| | | |
|---|---|---|
| 2004/0204379 A1 | 10/2004 | Cheng et al. |
| 2005/0130972 A1 | 6/2005 | Fan et al. |
| 2006/0079533 A1 | 4/2006 | Nieman et al. |
| 2008/0009516 A1 | 1/2008 | Wustman |

FOREIGN PATENT DOCUMENTS

| | | |
|---|---|---|
| WO | 199524391 A1 | 9/1995 |
| WO | 2004037233 A2 | 5/2004 |
| WO | 2008134628 A2 | 11/2008 |

OTHER PUBLICATIONS

International Search Report for PCT/US10/130472, dated Jun. 8, 2010.
European Search Report issued for co-pending European Patent Application No./Patent No. 10762469.4-1216/2416656; dated Aug. 2, 2012; Applicant: Amicus Therapeutics, Inc.

*Primary Examiner* — Jeffrey S Lundgren
*Assistant Examiner* — Meghan Finn
(74) *Attorney, Agent, or Firm* — SorinRand LLP (57) ABSTRACT

The present invention provides methods for preventing and/or treating lysosomal storage disorders using 5-(fluoromethyl)piperidine-3,4-diol, 5-(chloromethyl)piperidine-3,4-diol, or a pharmaceutically acceptable salt, solvate, or prodrug thereof, or any combination of two or more thereof. In particular, the present invention provides methods for preventing and/or treating Gaucher's disease.

18 Claims, 6 Drawing Sheets

METHODS FOR PREVENTING AND/OR TREATING LYSOSOMAL STORAGE DISORDERS

CROSS-REFERENCE TO RELATED APPLICATIONS

This application claims the benefit of U.S. Provisional Application No. 61/168,109, filed Apr. 9, 2009, the content of which is incorporated herein by reference.

FIELD OF THE INVENTION

The present invention provides methods for preventing and/or treating lysosomal storage disorders using 5-(fluoromethyl)piperidine-3,4-diol, 5-(chloromethyl)piperidine-3,4-diol, or a pharmaceutically acceptable salt, solvate or prodrug thereof, or any combination of two or more thereof. In particular, the present invention provides methods for preventing and/or treating Gaucher's disease.

BACKGROUND OF THE INVENTION

Lysosomal storage disorders are caused by a defect in lysosomal function that results in accumulation of substances within the lysosome of cells. This defect is usually a consequence of deficiency of a single enzyme required for the metabolism of lipid, glycogen, glycoprotein, or mucopolysaccharide. Gaucher's disease, the most common lysosomal storage disorder, is characterized by accumulation of the glycolipid glucocerebroside (also known as glucosylceramide). Symptoms of Gaucher's disease include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the sclera. In addition, persons affected with Gaucher's disease may also be more susceptible to infection.

There is a need for methods to prevent and/or treat lysosomal storage disorders that provide patients with a higher quality of life and achieve a better clinical outcome. In particular, there is a need for methods to prevent and/or treat Gaucher's disease that provide patients with a higher quality of life and achieve a better clinical outcome.

SUMMARY OF THE INVENTION

The present invention provides methods for preventing and/or treating a lysosomal storage disorder in a patient at risk for developing or diagnosed with the same, which comprises administering to the patient in need thereof an effective amount of a therapeutic agent which is 5-(fluoromethyl)piperidine-3,4-diol, 5-(chloromethyl)piperidine-3,4-diol, or a pharmaceutically acceptable salt, solvate, or prodrug thereof, or any combination of two or more thereof. In one embodiment, the method comprises administering 5-(fluoromethyl)piperidine-3,4-diol or a pharmaceutically acceptable salt, solvate, or prodrug thereof. In one embodiment, the method comprises administering (3R, 4R, 5R)-5-(fluoromethyl)piperidine-3,4-diol or a pharmaceutically acceptable salt, solvate, or prodrug thereof. In one embodiment, the method comprises administering (3R, 4R, 5R)-5-(fluoromethyl)piperidine-3,4-diol hydrochloride. In one embodiment, the method comprises administering 5-(chloromethyl)piperidine-3,4-diol or a pharmaceutically acceptable salt, solvate, or prodrug thereof. In one embodiment, the method comprises administering (3R, 4R, 5S)-5-(chloromethyl)piperidine-3,4-diol or a pharmaceutically acceptable salt, solvate, or prodrug thereof. In one embodiment, the method comprises administering (3R, 4R, 5S)-5-(chloromethyl)piperidine-3,4-diol. In one embodiment, the lysosomal storage disorder is associated with accumulation of at least one glycolipid. In one embodiment, the lysosomal storage disorder is associated with accumulation of at least one glycosphingolipid. In one embodiment, the lysosomal storage disorder is associated with accumulation of glucocerebroside. In one embodiment, the lysosomal storage disorder is associated with a deficiency in glucocerebrosidase. In one embodiment, the lysosomal storage disorder is associated with a mutation in glucocerebrosidase. In one embodiment, the lysosomal storage disease is Niemann-Pick disease. In one embodiment, the lysosomal storage disease is Gaucher's disease. In one embodiment, the method further comprises administering an effective amount of at least one other therapeutic agent. In one embodiment, the method comprises at least one other therapeutic agent is imiglucerase or 1,5-(butylimino)-1,5-dideoxy-D-glucitol.

The present invention also provides methods for preventing and/or treating Gaucher's disease in a patient at risk for developing or diagnosed with the same, which comprises administering to the patient in need thereof an effective amount of (3R, 4R, 5R)-5-(fluoromethyl)piperidine-3,4-diol, (3R, 4R, 5S)-5-(chloromethyl)piperidine-3,4-diol, or a pharmaceutically acceptable salt, solvate, or prodrug thereof, or any combination of two or more thereof. In one embodiment, the method comprises administering (3R, 4R, 5R)-5-(fluoromethyl)piperidine-3,4-diol or a pharmaceutically acceptable salt, solvate, or prodrug thereof. In one embodiment, the method comprises administering (3R, 4R, 5R)-5-(fluoromethyl)piperidine-3,4-diol hydrochloride. In one embodiment, the method comprises administering (3R, 4R, 5S)-5-(chloromethyl)piperidine-3,4-diol or a pharmaceutically acceptable salt, solvate, or prodrug thereof. In one embodiment, the method comprises administering (3R, 4R, 5S)-5-(chloromethyl)piperidine-3,4-diol. In one embodiment, the method further comprises administering an effective amount of at least one other therapeutic agent. In one embodiment, at least one other therapeutic agent is imiglucerase or 1,5-(butylimino)-1,5-dideoxy-D-glucitol.

The present invention also provides kits comprising:
 a container having an effective amount of 5-(fluoromethyl)piperidine-3,4-diol, 5-(chloromethyl)piperidine-3,4-diol, or a pharmaceutically acceptable salt, solvate, or prodrug thereof, or any combination of two or more thereof;
 instructions for using the same to prevent and/or treat a lysosomal storage disorder.

In one embodiment, the lysosomal storage disorder is Gaucher's disease.

The present invention also provide methods for enhancing the activity of glucocerebrosidase in a cell ex vivo using 5-(fluoromethyl)piperidine-3,4-diol, 5-(chloromethyl)piperidine-3,4-diol, or a pharmaceutically acceptable salt, solvate, or prodrug thereof, or any combination of two or more thereof. In addition, the present invention provides methods for diagnosing patients amenable to treatment comprising contacting ex vivo a cell from a patient at risk for developing or diagnosed with a lysosomal storage disorder with a therapeutic agent which is 5-(fluoromethyl)piperidine-3,4-diol, 5-(chloromethyl)piperidine-3,4-diol, or a pharmaceutically acceptable salt, solvate, or prodrug thereof, or any combination of two or more thereof and assaying a lysate of the cell for lysosomal glucocerebrosidase activity wherein an increase in lysosomal glucocerebrosidase activity relative to another cell that is not treated with the therapeutic agent indicates that the patient would be amenable to treatment. In one embodiment, the lysosomal storage disorder is Gaucher's disease.

DETAILED DESCRIPTION OF THE INVENTION

As used herein the following terms shall have the definitions set forth below.

As used herein the term "treating" means to ameliorate one or more symptoms associated with the referenced disorder.

As used herein, the term "preventing" means to mitigate a symptom of the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" means a mammal (e.g., a human).

As used herein the phrase "lysosomal storage disorder" refers to any of a group of diseases resulting from abnormal metabolism resulting in accumulation of a substrate in the lysosome. Table 1 contains a non-limiting list of exemplary lysosomal storage disorders and their associated defective enzyme.

TABLE 1

Lysosomal storage disorders

| Lysosomal storage disorder | Defective enzyme |
| --- | --- |
| Pompe disease | Acid α-glucosidase |
| Gaucher disease | Acid β-glucosidase or glucocerebrosidase |
| Fabry disease | α-Galactosidase A |
| $G_{M1}$-gangliosidosis | Acid β-galactosidase |
| Tay-Sachs disease | β-Hexosaminidase A |
| Sandhoff disease | β-Hexosaminidase B |
| Niemann-Pick disease | Acid sphingomyelinase |
| Krabbe disease | Galactocerebrosidase |
| Farber disease | Acid ceramidase |
| Metachromatic leukodystrophy | Arylsulfatase A |
| Hurler-Scheie disease | α-L-Iduronidase |
| Hunter disease | Iduronate-2-sulfatase |
| Sanfilippo disease A | Heparan N-sulfatase |
| Sanfilippo disease B | α-N-Acetylglucosaminidase |
| Sanfilippo disease C | Acetyl-CoA: α-glucosaminide N-acetyltransferase |
| Sanfilippo disease D | N-Acetylglucosamine-6-sulfate sulfatase |
| Morquio disease A | N-Acetylgalactosamine-6-sulfate sulfatase |
| Morquio disease B | Acid β-galactosidase |
| Maroteaux-Lamy disease | Arylsulfatase B |
| Sly disease | β-Glucuronidase |
| alpha.-Mannosidosis | Acid α-mannosidase |
| beta.-Mannosidosis Acid | β-mannosidase |
| Fucosidosis | Acid α-L-fucosidase |
| Sialidosis | Sialidase |
| Schindler-Kanzaki disease | α-N-acetylgalactosaminidase |

The most common lysosomal storage disorder, Gaucher's disease, is characterized by accumulation of the glycolipid glucocerebroside (also known as glucosylceramide). Three phenotypes have been described for Gaucher's disease that are denoted by the absence (type 1) or presence of neurologic involvement during childhood (type 2) or adolescence (type 3). For example, see Grabowski, Gaucher's disease. Adv Hum Genet. 1993; 21:377-441.

The three types of Gaucher's disease are inherited in an autosomal recessive fashion. Both parents must be carriers in order for a child to be affected. If both parents are carriers, there is a one in four, or 25%, chance with each pregnancy for an affected child. Genetic counseling and genetic testing is recommended for families who may be carriers of mutations. Each type has been linked to particular mutations. In all, there are about 80 known mutations that lead to Gaucher's disease (see, e.g., McKusick, V. A.: Mendelian Inheritance in Man. A Catalog of Human Genes and Genetic Disorders. Baltimore: Johns Hopkins University Press, 1998 (12th edition)).

Type 1 Gaucher's disease is panethnic, but is especially prevalent among persons of Ashkenazi Jewish descent, with a carrier rate of 1 in 17 Ashkenazi Jews. The N370S and 84GG mutations are the most frequent mutations in the glucocerebrosidase gene among Ashkenazi Jews, with rates of 1 in 17.5 for N370S and 1 in 400 for 84GG in the general healthy Ashkenazi population, and are associated with mild and severe Gaucher's disease, respectively. The 84GG mutation occurs almost exclusively among Ashkenazi Jews. Other rare glucocerebrosidase gene variants identified in patients of Ashkenazi descent with Gaucher's disease include L444P, IVS2+1G→A, V394L, and R496H. In contrast to presentation of Type 1 Gaucher's disease in Ashkenazi Jews, Type 1 Gaucher's disease tends to be severe and progressive in Japanese patients (see, Ida et al., Type 1 Gaucher Disease Patients: Phenotypic Expression and Natural History in Japanese Patients, Blood Cells, Molecules and Diseases, 1984, 24(5): 73-81). In addition, Type 3 Gaucher's disease, associated with one or two copies of glucocerebrosidase gene variant L444P is prevalent in Swedish patients from the Norrbotten region.

A definitive diagnosis of Gaucher's disease is made with genetic testing. As there are numerous different mutations, sequencing of the glucocerebrosidase gene is sometimes necessary to confirm the diagnosis. Prenatal diagnosis is available, and is useful when there is a known genetic risk factor. However, a diagnosis of Gaucher's disease can also be implied by biochemical abnormalities such as high alkaline phosphatase, angiotensin-converting enzyme (ACE) and immunoglobulin levels, or by cell analysis showing "crinkled paper" cytoplasm and glycolipid-laden macrophages. Notably, Niemann-Pick disease is similar in that it is characterized by accumulation of $G_{M2}$-gangliosides and $G_{M1}$-gangliosides in addition to glucocerebroside (Vanier et al., *Brain Pathology*. 1998; 8: 163-74).

Symptoms of Gaucher's disease include the following:

Painless hepatomegaly and splenomegaly (the size of the spleen can be 1500-3000 ml, as opposed to the normal size of 50-200 ml)

Hypersplenism: the rapid and premature destruction of blood cells, leading to anemia, neutropenia and thrombocytopenia (with an increased risk of infection and bleeding)

Cirrhosis of the liver, though rare

Neurological symptoms occur only in some types of Gaucher's (see below):

Type II: serious convulsions, hypertonia, mental retardation, apnea.

Type III: muscle twitches known as myoclonus, convulsions, dementia, ocular muscle apraxia.

Osteoporosis: 75% develop visible bony abnormalities due to the accumulated glucosylceramide. A deformity of the distal femur in the shape of an Erlenmeyer flask is commonly described Yellowish-brown skin pigmentation.

Chemical Syntheses a. Isofagomine (IFG; (3R,4R,5R)-5-(hydroxymethyl)-3,4-piperidinediol))

Isofagomine (IFG; (3R,4R,5R)-5-(hydroxymethyl)-3,4-piperidinediol)) refers to a compound having the following structure:

Synthesis of isofagomine is described in U.S. Pat. Nos. 5,844,102 to Sierks et al. at column 17, line 53 to column 20, line 6, incorporated herein by reference and 5,863,903 to Lundgren et al. in Example 1, at column 5, line 20 to column 7, line 33, incorporated herein by reference. Isofagomine tartrate, also known as IFG and Plicera™, has been assigned CAS number 919364-56-0. Preparation of isofagomine tartrate is described in US2007/02819751 at paragraphs [0046] to [0050] and purification of isofagomine tartrate is described at paragraphs [0051] to [0053], both of which are specifically incorporated herein by reference.

b. Synthesis of (3R,4R,5R)-5-(fluoromethyl)piperidine-3,4-diol hydrochloride (4aR,8R,8aR)-6-benzyl-2,2-dimethylhexahydro-4H-[1,3]dioxino[5,4,c]pyridin-8-ol (2).

To a solution of (3R,4R,5R-5-(hydroxymethyl)piperidine-3,4-diol (1) (5.9 g, 40.0 mmol) in dry DMF (75 mL) was added K$_2$CO$_3$ (6.4 g, 46.0 mmol) followed by benzyl chloride (4.8 mL, 42.0 mmol) and the resulting mixture was heated to 70° C. for 14 hrs at which point the starting material could not be detected by tlc. The solvent was evaporated in vacuo and the residue was redissolved in a minimum amount of water. The solution was extracted 10-12× with EtOAc and the combined extracts were dried over Na$_2$SO$_4$ and filtered. The filtrate was evaporated in vacuo to give the title compound (7.5 g, 79%) as a tan solid which could be used without further purification. The tan solid was dissolved in DMF (75 mL) and toluenesulfonic acid (6.7 g, 35.0 mmol) was added followed by 2-methoxy propene (7.2 mL, 75.0 mmol) and the mixture was stirred overnight at room temperature. After stirring overnight an additional 7.2 mL of 2-methoxy propene was added and the mixture was again stirred overnight at room temperature. At this point no starting material could be detected by tlc.

Sodium hydroxide (50% aq, 5 mL) was added to the reaction mixture and the solvent was evaporated in vacuo. The residue was dissolved in EtOAc and washed with water. The aqueous washes were combined and washed 1× with EtOAc. This was combined with original extracts, washed with brine and dried over MgSO$_4$. The solution was filtered and the solvent evaporated to give a waxy solid. This solid can be directly used in the next step. An analytical sample can be obtained from chromatography (0 to 5% (9/1 MeOH/NH$_4$OH) in CHCl$_3$) to obtain the title compound. $^1$H NMR (CDCl$_3$) 1.35 (s, 3H), 1.39 (s, 3H), 1.66 (t, 1H), 1.83 (m, 1H), 1.95 (t, 1H), 2.56 (ddd, 1H), 3.03 (ddd, 1H), 3.30 (t, 1H), 3.6-3.8 (m, 5H), 7.27 (m, 5H).

(3R,4R,5R)-1-benzyl-3-(benzyloxy)-5-(hydroxymethyl)piperidin-4-ol (3).

To a solution of 2 (4.4 g, 15.9 mmol) in DMF (50 mL) was added 95% NaH (0.43 g, 17.9 mmol) and the resulting mixture was stirred 1 hr under N$_2$. Then benzyl chloride (1.9 mL, 16.3 mmol) was added and the mixture was stirred overnight at room temperature. After approximately 14 hrs the DMF was evaporated in vacuo. The residue was dissolved in EtOAc and washed with water and then brine and then dried over MgSO$_4$. The solution was filtered and the filtrate evaporated in vacuo to give the crude product. Chromatography on silica gel eluting with 0-25% EtOAc/hexane gave 2.1 g of a white foam. $^1$H NMR (CDCl$_3$) 1.15 (m, 1H), 1.19 (s, 3H), 1.39 (s, 3H), 1.9-2.05 (m, 4H), 2.53 (ddd, 1H), 3.04 (ddd, 1H), 3.3 (s, 1H), 3.45-3.8 (m, 4H), 7.2 (m, 10H). This was dissolved in MeOH (100 mL) and 1.5 mL of 6N HCl in 2-PrOH was added and the mixture was stirred at room temperature. After 1 hr the starting material was gone as judged by tlc. The solvent was evaporated and the residue was dissolved in 10% Na$_2$CO$_3$ and extracted with EtOAc (2×). The combined extracts were washed with one small portion of water and then brine and dried over MgSO$_4$. The solution was filtered and the filtrate was evaporated to give the title compound (1.7 g, 33%). $^1$H NMR (CDCl$_3$) 1.6-1.95 (m, 3H), 2.63 (ddd, 1H), 3.00 (ddd, 1H), 3.25-3.65 (m, 5H), 4.35 (d, 1H), 4.5 (d, 1H), 7.2 (m, 10H).

((3R,4R,5R)-1-benzyl-4,5-bis(benzyloxy)-piperidin-3-yl)methanol (4b).

To a solution of 3 (1.1 g, 3.36 mmol) in DMF (10 mL), was added NaH (0.10 g, 4.0 mmol) and the reaction was stirred 30 minutes at room temperature at which point benzyl chloride (0.38 mL, 3.3 mmol) was added and the reaction was stirred overnight at room temperature. The solvent was evaporated in vacuo and the residue was dissolved in EtOAc and washed with water and then brine and dried over Na$_2$SO$_4$. The solution was filtered and the filtrate evaporated to give a mixture of 4a and 4b (roughly a 2/1 mixture). The mixture was chromatographed on silica gel eluting with 0-50% EtOAc/hexane. The fractions corresponding to the major regioisomer were combined to give 4a (0.49 g, 35%) as a colorless oil. $^1$H NMR (CDCl$_3$) 1.81 (t, 2H), 1.96 (m, 1H), 2.80 (m, 1H), 3.05 (ddd, 1H), 3.3-3.6 (m, 6H), 4.41 (s, 2H), 4.55 (q, 2H), 7.2 (m, 15H). The fractions of the minor regioisomer were combined to give 4b (0.23 g, 16%) as a colorless oil. $^1$H NMR (CDCl$_3$) 1.8-2.0 (m, 3H), 2.72 (dd, 1H), 3.05 (ddd, 1H), 3.27 (t, 1H), 3.4-3.6 (m, 4H), 3.65 (m, 1H), 4.56 (s, 2H), 4.60 (d, 1H), 4.90 (d, 1H), 7.2 (m, 15H).

(3R,4R,5R)-1-benzyl-3,4-bis(benzyloxy)-5-(fluoromethyl)piperidin-4-ol (5).

A solution of 4b (0.32 g, 0.77 mmol) in CH$_2$Cl$_2$ (40 mL) was cooled to −15 to −20° C. in an ice/salt water bath. To this was added (diethylamino)sulfur trifluoride (0.15 mL, 1.15 mmol) and the reaction was allowed to stir for about 20 minutes at which point the starting material was consumed as judged by tlc. The reaction was quenched by the addition of NaHCO$_3$ and the mixture was extracted with EtOAc (2×). The combined extracts were washed with brine and then dried over Na$_2$SO$_4$. The solution was filtered and the filtrate was evaporated to give the crude product. Silica gel chromatography (0-25% EtOAc/hexane) afforded the desired product (0.2 g, 63%) as a colorless oil. $^1$H NMR (CDCl$_3$) 1.9-2.15 (m, 3H), 2.88 (dd, 1H), 3.12 (ddd, 1H), 3.36 (t, 1H), 3.55 (d, 1H), 3.65 (m, 1H), 4.3-4.6 (m, 3H), 4.63-4.65 (m, 3H), 4.95 (d, 1H), 7.2 (m, 15H).

(3R,4R,5R)-5-(fluoromethyl)piperidine-3,4-diol hydrochloride(6).

To a solution of 5 (0.24 g, 0.57 mmol) in EtOH (40 mL) was added 0.5 mL of 6N HCl in 2-PrOH. The solvent was evaporated in vacuo and then co-evaporated 2× more with EtOH. The residue was dissolved in EtOH and hydrogenated at 55 psi using Pd(OH)$_2$ as catalyst. After 14 hrs the starting material could no longer be detected and the solution was filtered and the filtrate was evaporated in vacuo. The residue was triturated with acetone and then filtered to give an off white solid (0.09 g, 85%) as the title compound. $^1$H NMR (DMSO-d$_6$) 1.95-2.05 (m, 1H), 2.65 (t, 1H), 2.85 (t, 1H) 3.15-3.4 (m, 3H), 3.55 (m, 1H), 4.55 (m, 1H), 4.65 (m, 1H), 5.45-5.6 (dd, 2H), 9.05 (br s, 2H).

(3R,4R,5R)-5-(fluoromethyl)piperidine-3,4-diol hydrochloride(6).

To a solution of 7 (7.5 g, 22.8 mmol) in EtOH (150 mL) was added 5N HCl in 2-PrOH (7 mL). The solution was evaporated in vacuo, then co-evaporated 2× more with EtOH. The resulting material was dissolved in EtOH (100 mL) and the resulting solution was hydrogenated overnight with Pd(OH)$_2$ at 50 psi. The catalyst was removed by filtration and the filtrate was evaporated in vacuo. The residue was triturated with acetone and a pale yellow solid was collected. The resulting solid was recrystallized from EtOH to give the title compound as an off-white solid mp 200-202° C. $^1$H NMR DMSO d$_6$ consistent with previous spectra.

c. Synthesis of (3R,4R,5R)-5-(fluoromethyl)piperidine-3,4-diol

One approach for obtaining the free base of (3R,4R,5R)-5-(fluoromethyl)piperidine-3,4-diol is to synthesize (3R,4R,5R)-5-(fluoromethyl)piperidine-3,4-diol hydrochloride as described in section "b" above followed by chromatography of (3R,4R,5R)-5-(fluoromethyl)piperidine-3,4-diol hydrochloride using 5-15% MeOH/NH$_4$OH (9:1) in CHCl$_3$ which converts the HCl salt form of (3R,4R,5R)-5-(fluoromethyl)piperidine-3,4-diol to its free base.

d. Synthesis of (3R,4R,5S)-5-(chloromethyl)piperidine-3,4-diol (3R,4R,5R)-1-benzyl-3-(benzyloxy)-5-(fluoromethyl)piperidin-4-ol (7).

To a solution of 3 (26.0 g, 79.5 mmol) dissolved in pyridine (300 mL) and cooled in an ice bath was added TsCl (16.6 g, 87.5 mmol) in portions. After the addition was complete, the reaction mixture was allowed to warm to room temperature and stirred overnight. The solvent was evaporated in vacuo and the residue dissolved in EtOAc. The solution was washed with water (2×) and then brine and then dried over MgSO$_4$. The solution was filtered and the filtrate evaporated in vacuo to give the crude product which was dried under high vacuum. The residue was dissolved in THF (400 mL) and 1.0 M Bu$_4$NF (100 mmol, 100 mL0 was added and the mixture was heated at reflux. After 2 hrs, there was no starting material remaining. The reaction mixture was diluted with EtOAc and washed with water (2×) and then with brine and dried over MgSO$_4$. The solution was filtered and the filtrate was evaporated in vacuo. The crude product was purified by silica gel chromatography (25% EtOAc/hexane) to give the title compound (7.5 g, 29% for 2 steps).

(1)

(2)

(2S,3S,4aR,8S,8aR)-6-benzyl-8-(chloromethyl)-2,3-dimethoxy-2,3-dimethyloctahydro-[1,4]dioxino[2,3-c]pyridine (2).

To a solution of ((2S,3S,4aR,8R,8aR)-6-benzyl-2,3-dimethoxy-2,3-dimethyloctahydro-[1,4]dioxino[2,3-c]pyridine-8-yl)methanol (1) (2.5 g, 7.1 mmol) in chloroform (35 mL) was added thionyl chloride (1.3 mL, 18 mmol). The resulting mixture was heated at reflux for 4-8 hours until reaction was judged complete by TLC (98:2 CH$_2$Cl$_2$/2-PrOH). Solvent and excess reagent were evaporated in vacuo and the residue was chromatographed (98:2 CH$_2$Cl$_2$/2-PrOH) to give the title compound (2.2 g, 85%). Product was characterized via HPLC/MS (MH$^+$=369). Purity was judged as >95%.

(3R,4R,5S)-1-benzyl-5-(chloromethyl)piperidine-3,4-diol (3).

To a solution of (2S,3S,4aR,8S,8aR)-6-benzyl-8-(chloromethyl)-2,3-dimethoxy-2,3-dimethyloctahydro-[1,4]dioxino[2,3-c]pyridine (2) (2.2 g, 5.9 mmol) in dichloromethane (15 mL) was added trifluoroacetic acid (0.35 mol, 26 mL). Reaction mixture was heated at reflux for about 1 hour at which point reaction was judged complete by TLC. Excess solvent and TFA were evaporated in vacuo and the residue was chromatographed using silica gel (2-8% MeOH in CHCl$_3$). Fractions were combined and evaporated to give (1.3 g, 87%) as the title compound. Product was characterized via HPLC/MS (MH$^+$=255) and judged to be >95% pure.

(3R,4R,5S)-5-(chloromethyl)piperidine-3,4-diol (4).

5N HCl (4.7 mmol, 0.94 mL) was added to (3R,4R,5S)-1-benzyl-5-(chloromethyl)piperidine-3,4-diol (3) (5.1 mmol, 1.3 g) dissolved in EtOH. Solution was evaporated in vacuo and then co-evaporated 2-3× with EtOH. The residue was redissolved in EtOH and combined with Pd(OH)$_2$ (0.27 g), and hydrogenated at 55 psi for 12 hrs. The catalyst was subsequently filtered through dicalite and the filtrate was evaporated to obtain crude (4) as an HCl salt. This was then chromatographed (5-15% MeOH/NH$_4$OH (9:1) in CHCl$_3$) to give 0.4 g of (4) as a white solid with. MH$^+$ of 165 and $^1$H NMR (DMSO-d$_6$) 1.6 (m, 1H), 2.2 (m, 3H), 2.9 (m, 3H), 3.15 (m, 1H), 3.6(m, 1H), 3.8 (dd, 1H), 4.68 (d, 1H), 4.88 (d, 1H).

e. Synthesis of (3R,4R,5S)-5-(chloromethyl)piperidine-3,4-diol hydrochloride

One approach for obtaining the hydrochloride salt of (3R,4R,5S)-5-(chloromethyl)piperidine-3,4-diol is to synthesize (3R,4R,5S)-5-(chloromethyl)piperidine-3,4-diol as described in section "d" above followed by reacidification with HCl (either as an aqueous solution or in 2-PrOH as it is often sold) whereby the free base is converted to the HCl salt form of (3R,4R,5S)-5-(chloromethyl)piperidine-3,4-diol and subsequent isolation of (3R,4R,5S)-5-(chloromethyl)piperidine-3,4-diol hydrochloride.

Alternatively, the synthesis of (3R,4R,5S)-5-(chloromethyl)piperidine-3,4-diol may be followed as described in section "d" above with the exception of the last chromatographic step whereby the HCl salt is chromatographed using 5-15% MeOH/NH$_4$OH (9:1) in CHCl$_3$ as this step results in the conversion of the crude HCl salt form of (3R,4R,5S)-5-(chloromethyl)piperidine-3,4-diol to the free base. Rather, the crude HCl salt form of (3R,4R,5S)-5-(chloromethyl)piperidine-3,4-diol may be purified by crystallization.

Salts, Solvates and Prodrugs

Compounds of the present invention include pharmaceutically acceptable salts, solvates and pro-drugs of (3R,4R,5R)-5-(fluoromethyl)piperidine-3,4-diol (also referred to herein as Compound A) and (3R,4R,5S)-5-(chloromethyl)piperidine-3,4-diol (also referred to herein as Compound B). Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, hydrochlorides, sulphates, nitrates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. In one embodiment, the pharmaceutically acceptable salt of (3R,4R,5R)-5-(fluoromethyl)piperidine-3,4-diol is the hydrochloride salt (also referred to herein Compound A-HCl).

"Solvate" denotes a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. "Hydrate" is a solvate wherein the solvent molecule is H$_2$O. Other non-limiting examples of suitable solvates include alcohols (e.g., ethanolates, methanolates, and the like).

Prodrugs are compounds which are converted in vivo to active forms (see, e.g., R. B. Silverman, 1992, "The Organic Chemistry of Drug Design and Drug Action", Academic Press, Chapter 8, incorporated herein by reference). Additionally, a discussion of prodrugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference thereto. Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound with a suitable derivatizing agent. For example hydroxy groups can be converted into esters via treatment with a carboxilic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

All stereoisomers (for example, geometric isomers, optical isomers and the like) of 5-(fluoromethyl)piperidine-3,4-diol and 5-(chloromethyl)piperidine-3,4-diol (including those of the salts, solvates and prodrugs of these compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of these compounds may, for example, be substantially free of other isomers, or may be admixed, for example, as racemates or with all other, or other selected, stereoisomers. The chiral centers of the aforementioned compounds can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of 5-(fluoromethyl)piperidine-3,4-diol and 5-(chloromethyl)piperidine-3,4-diol.

Formulations

The therapeutic agent(s) can be formulated to be suitable for any route of administration, including e.g., orally in the form of tablets or capsules or liquid, or in sterile aqueous solution for injection. When the therapeutic agent(s) is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the therapeutic agent(s).

In certain embodiments of the present invention, the therapeutic agent(s) is administered in a dosage form that permits systemic uptake, such that the therapeutic agent(s) may cross the blood-brain barrier so as to exert effects on neuronal cells. For example, pharmaceutical formulations of the therapeutic agent(s) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the therapeutic agent(s) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Routes of Administration

The therapeutic agent(s) may be administered orally or parenterally, including intravenously, subcutaneously, intraarterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodible implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

A suitable pharmaceutical preparation is in a unit dosage form. In such form, the preparation is subdivided into suitably sized unit doses containing appropriate quantities of the active component, e.g., an effective amount to achieve the desired purpose. In certain embodiments, the therapeutic agent(s) is administered in one or more daily doses (e.g., once-a-day, twice-a-day, thrice-a-day). In certain embodiments, the therapeutic agent(s) is administered in intermittently.

Exemplary dosing regimens are described in International patent application PCT/US08/61764 published as WO 2008/134628 on Jun. 11, 2008 and U.S. patent application Ser. No. 12/604,855, filed on Oct. 23, 2009, both of which are incorporated by reference herein in their entirety. In one embodiment, the therapeutic agent(s) is administered in an intermittent dosing regimen that includes an initial "loading dose" given daily, followed by a period of non-daily interval dosing.

The amount of effective therapeutic agent(s) for preventing or treating the referenced disorder can be determined on a case-by-case basis by those skilled in the art. The amount and frequency of administration of the therapeutic agent(s) will be regulated according to the judgment of the attending clinician (physician) considering such factors as age, condition and size of the patient as well as risk for developing disorder or severity of the symptoms of the referenced disorder being treated.

Combination Drug Therapy

The therapeutic agent(s) of the present invention can be administered in combination with at least one other therapeutic agent. Administration of the therapeutic agent(s) of the present invention with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

In certain embodiments, the therapeutic agent(s) of the present invention are administered in combination with at least one other therapeutic agent which is an anti-dyskinesia Agent (e.g., Carbidopa, Levodopa), an anti-infective agent (e.g., Miglustat), an antineoplastic agent (e.g., Busulfan, Cyclophosphamide), a gastrointestinal agent (e.g., Methylprednisolone), a micronutrient (e.g., Calcitriol, Cholecalciferol, Ergocalciferols, Vitamin D), a vasoconstrictor agent (e.g., Calcitriol). In one preferred embodiment, the aforementioned other therapeutic agents are administered when the disorder is Gaucher's disease.

In certain embodiments, the therapeutic agent(s) of the present invention are administered in combination with allopregnanolone, a low-cholesterol diet, or cholesterol-lowering agents such as statins (e.g., Lipitor®); fibrates such as fenofibrate (Lipidil®); niacin; and/or binding resins such as cholestyramine (Questran®).

In one embodiment, the therapeutic agent(s) of the present invention is administered in combination with gene therapy. Gene therapy is contemplated both with replacement genes such as glucocerebrosidase or with inhibitory RNA (siRNA) for the SNCA gene. Gene therapy is described in more detail in U.S. Pat. No. 7,446,098, filed on Feb. 17, 2004.

In one embodiment, the therapeutic agent(s) of the present invention is administered in combination with at least one other therapeutic agent which is an anti-inflammatory agent (e.g., ibuprofen or other NSAID).

In one embodiment, the therapeutic agent(s) of the present invention is administered in combination with a substrate inhibitor for glucocerebrosidase, such as N-butyl-deoxynojirimycin (Zavesca®; miglustat available from Actelion Pharmaceuticals, US, Inc., South San Francisco, Calif., US).

Combinations of the therapeutic agent(s) of the present invention with at least one other therapeutic agent which is a therapeutic agent for one or more other lysosomal enzymes are also contemplated. Table 2 contains a non-limiting list of therapeutic agents for lysosomal enzymes.

TABLE 2

| LYSOSOMAL ENZYME | THERAPEUTIC AGENT |
|---|---|
| α-Glucosidase<br>GenBank Accession No. Y00839 | 1-deoxynojirimycin (DNJ)<br>α-homonojirimycin<br>castanospermine |
| Acid β-Glucosidase (β-glucocerebrosidase)<br>GenBank Accession No. J03059 | isofagomine<br>C-benzyl isofagomine and derivatives<br>N-alkyl (C9-12)-DNJ<br>Glucoimidazole (and derivatives)<br>C-alkyl-IFG (and derivatives)<br>N-alkyl-β-valeinamines<br>Fluphenozine<br>calystegines $A_3$, $B_1$, $B_2$ and $C_1$ |
| α-Galactosidase A<br>GenBank Accession No. NM000169 | 1-deoxygalactonojirimycin (DGJ)<br>α-allo-homonojirimycin |

TABLE 2-continued

| LYSOSOMAL ENZYME | THERAPEUTIC AGENT |
|---|---|
| | α-galacto-homonojirimycin |
| | β-1-C-butyl-deoxynojirimycin |
| | calystegines A$_2$ and B$_2$ |
| | N-methyl calystegines A$_2$ and B$_2$ |
| Acid β-Galactosidase | 4-epi-isofagomine |
| GenBank Accession No. M34423 | 1-deoxygalactonojirimyicn |
| Galactocerebrosidase (Acid β-Galactosidase) | 4-epi-isofagomine |
| GenBank Accession No. D25283 | 1-deoxygalactonojirimycin |
| Acid α-Mannosidase | 1-deoxymannojirimycin |
| GenBank Accession No. U68567 | Swainsonine |
| | Mannostatin A |
| Acid β-Mannosidase | 2-hydroxy-isofagomine |
| GenBank Accession No. U60337 | |
| Acid α-L-fucosidase | 1-deoxyfuconojirimycin |
| GenBank Accession No. NM_000147 | β-homofuconojirimycin |
| | 2,5-imino-1,2,5-trideoxy-L-glucitol |
| | 2,5-deoxy-2,5-imino-D-fucitol |
| | 2,5-imino-1,2,5-trideoxy-D-altritol |
| α-N-Acetylglucosaminidase | 1,2-dideoxy-2-N-acetamido-nojirimycin |
| GenBank Accession No. U40846 | |
| α-N-Acetylgalactosaminidase | 1,2-dideoxy-2-N-acetamido-galactonojirimycin |
| GenBank Accession No. M62783 | |
| β-Hexosaminidase A | 2-N-acetylamino-isofagomine |
| GenBank Accession No. NM_000520 | 1,2-dideoxy-2-acetamido-nojirimycin Nagstatin |
| β-Hexosaminidase B | 2-N-acetamido-isofagomine |
| GenBank Accession No. NM_000521 | 1,2-dideoxy-2-acetamido-nojirimycin Nagstatin |
| α-L-Iduronidase | 1-deoxyiduronojirimycin |
| GenBank Accession No. NM_000203 | 2-carboxy-3,4,5-trideoxypiperidine |
| β-Glucuronidase | 6-carboxy-isofagomine |
| GenBank Accession No. NM_000181 | 2-carboxy-3,4,5-trideoxypiperidine |
| Sialidase | 2,6-dideoxy-2,6, imino-sialic acid |
| GenBank Accession No. U84246 | Siastatin B |
| Iduronate sulfatase | 2,5-anhydromannitol-6-sulphate |
| GenBank Accession No. AF_011889 | |
| Acid sphingomyelinase | desipramine, phosphatidylinositol-4,5-diphosphate |
| GenBank Accession No. M59916 | |

In certain embodiments, the therapeutic agent(s) of the present invention are administered in combination with at least one therapeutic agent which is an anti-dyskinesia Agent (e.g., Carbidopa, Levodopa), an anti-infective agent (e.g., Cyclosporine, Miglustat, Pyrimethamine), an antineoplastic agent (e.g., Alemtuzumab, Azathioprine, Busulfan, Clofarabine, Cyclophosphamide, Melphalan, Methotrexate, Rituximab), an antirheumatic agent (e.g., Rituximab) a gastrointestinal agent (e.g., Methylprednisolone), a micronutrient (e.g., Calcitriol, Cholecalciferol, Ergocalciferols, Folic Acid, Vitamin D), a reproductive control agent (e.g., Methotrexate), a respiratory system agent (e.g., Tetrahydrozoline), vasoconstrictor agent (e.g., Calcitriol, Tetrahydrozoline).

In certain embodiments, the therapeutic agent(s) of the present invention are administered in combination with at least one therapeutic agent which is a therapeutic agent for β-hexosaminidase A and/or a therapeutic agent for acid β-galactosidase. In certain embodiments, the therapeutic agent(s) of the present invention are administered in combination with at least one therapeutic agent which is an anti-infective agent (e.g., Miglustat), antineoplastic agent (e.g., Alemtuzumab, Busulfan, Cyclophosphamide), a gastrointestinal agent (e.g., Methylprednisolone). In one embodiment, the aforementioned combination is administered to subjects at risk or diagnosed with Niemann-Pick disease (e.g., Niemann-Pick disease type C).

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Determination of Inhibition Constants

The binding affinity (defined here by $K_i$ binding constant) of GCase for small molecule pharmacological chaperones described in this document were empirically determined using enzyme inhibition assays. In brief, the enzyme inhibition assays used monitored the ability of test compound to bind and prevent the hydrolysis of a fluorogenic substrate in a concentration-dependent manner. Specifically, the enzyme activity of recombinant human GCase (rhGCase; Cerezyme®, Genzyme Corp.) was measured using the 4-methylumbelliferyl-β-D-glucopyranoside (4-MU-β-D-Glc) fluorogenic substrate in the absence or in the presence of varying amounts of each test compound. The resultant data were analyzed by comparing all test samples to the no inhibition control sample (no compound; corresponding to 100% enzyme activity) to determine the residual enzyme activity in the presence of test compound. The normalized residual activity data were subsequently graphed (on y-axis) relative to the concentration of test compound (on x-axis) to extrapolate the test compound concentration which leads to 50% inhibition of enzyme activity (defined as IC$_{50}$). The IC$_{50}$ value for each test compound was then inserted into the Cheng-Prusoff equation (detailed below) to derive the absolute inhibition constant K$_i$ that accurately reflects the binding affinity of GCase for the test compound. The enzyme inhibition assays were performed at both pH 7.0 (endoplasmic reticulum pH) and at pH 5.2 (lysosomal pH) to gain insight into the binding affinity (i.e., potency) of compounds for GCase in the endoplasmic reticulum and lysososome.

In Vitro Assay

Various concentrations of test compounds were prepared in buffer "M" consisting of 50 mM sodium phosphate buffer with 0.25% sodium taurocholate at pH 7.0 and pH 5.2. Enzyme (Cerezyme®, a recombinant form of the human enzyme β-glucocerebrosidase) was also diluted in the same buffer "M" at pH 7.0 and pH 5.2. The substrate solution consisted of 3 mM 4-methylumbelliferone β-D-glucopyranoside in buffer "M" with 0.15% Triton X-100 at both pH's. Five µl of diluted enzyme was added to 15 µl of the various inhibitor concentrations or buffer "M" alone and incubated at 37° C. for 1 hour with 50 µl of the substrate preparation to assess β-glucosidase activity at pH 7.0 and pH 5.2. Reactions were stopped by addition of an equal volume of 0.4 M glycine, pH 10.6. Fluorescence was measured on a plate reader for 1 sec/well using 355 nm excitation and 460 nm emission. Incubations without added enzyme or without added inhibitors were used to define no enzyme activity and maximum activity, respectively, and normalize % inhibition for a given assay. The results of this inhibition assay for reference compound, IFG-tartrate, and test compounds, the hydrochloride salt form of Compound A and Compound B, are summarized below in Table 2A.

chloride salt form of Compound A and Compound B, enhanced enzyme activity to the same maximum level at much lower concentration.

TABLE 2A

In vitro Determination of Inhibition Constants

| Compound | $IC_{50}$ (mM) pH 5.2 | Ki (µM) pH 5.2 | $IC_{50}$ (µM) pH 7 | Ki (µM) pH 7 |
|---|---|---|---|---|
| IFG-Tartrate | 0.0437 ± 0.0018 | 0.023 ± 0.001 | 0.00626 ± 0.00018 | 0.0033 ± 0.00013 |
| Compound A-HCl | 0.014 ± 0.006 | 0.006 ± 0.003 | 0.006 ± 0.0005 | 0.003 ± 0.0003 |
| Compound A-HCl* | 0.014 ± 0.001 | 0.006 ± 0.0004 | 0.007 ± 0.0004 | 0.004 ± 0.0002 |
| Compound B | 0.0729 ± 0.004 | 0.384 ± 0.0021 | 0.0098 ± 0.0005 | 0.0051 ± 0.0003 |

Note:
*independent synthesis of the hydrochloride salt form of Compound A

In Situ Assay

The effect of IFG and its derivatives on lysosomal GCase activity was assayed in situ using fibroblasts established from a normal subject. Cells seeded in 48-well plates were incubated with the indicated concentrations of compound for 16-24 hours. For the dose-response assays, cells were incubated with the in situ substrate 5-(pentafluorobenzoylamino) fluorescein di-β-D-glucopyranoside (PFBFDβGlu) for 1 hour and subsequently lysed to determine the extent of substrate hydrolysis in the presence of compound. The assay employed a range of 12 concentrations encompassing 5 orders of magnitude, centered on the IC50. Specifically, the following concentration ranges were employed: Compound A: $1\times10^{-5}$ to $3.33\times10^{-11}$; IFG: $3.33\times10^{-5}$ to $1\times10^{10}$; Compound B: $3\times10^{-5}$ to $9\times10^{-11}$; wherein compound was serially diluted 1:3 from the highest concentration in the ranges specified. Inhibition was determined as the ratio of activity in the presence of compound to that in the absence of compound. For the washout assays, cells were treated with compound for 16-24 hours at a concentration equal to the IC90. Cells were washed extensively and incubated in drug-free medium to allow net compound efflux from cells. Cells were then tested for lysosomal GCase activity at 2 hour intervals over a total period of 8 hours following compound removal. The increase in activity over time was fitted with a single exponential function to determine the compound's washout time. The results of these inhibition assays are summarized below in Table 2B.

Example 2

Blood Brain Barrier Penetration

The blood-brain barrier (BBB) penetration of reference compound (IFG-tartrate) and test compounds (IFG-derivatives, the hydrochloride salt form of Compound A and Compound B) were assayed after oral administration to mice. For this purpose, 8-week old wild-type male mice (C57BL/6) were administered a single 30 mg/kg (free base equivalent) p.o. dose of reference or test compound by gavage (n=3 mice per time point). Dosing solutions were prepared in water. After dosing, mice were euthanized with $CO_2$ at the following time points: 0-, 0.5-, 1-, and 4-hour post-dose. After euthanization, whole blood was collected from the inferior vena cava into lithium heparin tubes. Similarly, brains were collected from each mouse. Plasma was derived by spinning whole blood at 2700 g for 10 minutes at 4° C. followed by storage on dry ice. Whole brains were washed in cold PBS to remove contaminating blood, blotted dry, flash frozen on dry ice, and ultimately stored at −80° C. until analysis. To prepare brain samples for analysis, 50-100 mg of tissue was homogenized in 400 µl of water/mg tissue. Samples were then clarified by centrifugation. Next, 25 µl of the brain homogenate supernatant or 25 µl of plasma were combined with 25 µl of acetonitrile:water (95/5). This was supplemented with 25 µl of acetonitrile and 50 µL of internal standard (100 ng/mL IFG 13C2-15N in 0.5% formic acid in (70:30) acetonitrile:methanol.

TABLE 2B

In situ Determination of Inhibition Constants

| Compound | In Situ $IC_{50}$ (µM) | In Situ Washout (hr) | $EC_{50}$ (µM) | Emax (%) |
|---|---|---|---|---|
| IFG-Tartrate | 0.271 ± 0.012 | 8.2 ± 0.04 | 0.9 ± 0.2 | 93.6 ± 2.5 |
| Compound A-HCl | 0.017 ± 0.008 | 6.6 ± 0.12 | 0.00138 ± 0.00063 | 96.8 ± 7.7 |
| Compound A-HCl* | | | 0.0056 ± 0.0015 | 104 ± 4.58 |
| Compound B | 0.121 ± 0.007 | 2.9 ± 0.22 | 0.0096 ± 0.001 | 104.2 ± 3.4 |

Notes:
*independent synthesis of the hydrochloride salt form of Compound A
Cheng-Prusoff equation: $Ki = IC_{50}/(1 + [S]/K_m)$
where [S] = substrate concentration; 2.5 mM 4-MU-β-D-Glc was used
$K_m$ = Michaelis constant that defines substrate affinity; 1.8 ± 0.6 mM for 4-MU-β-D-Glc (Liou et al., (2006) J Biol. Chem. 281 (7), 4242-53)

Notably, test compounds, the hydrochloride salt form of Compound A and Compound B, were found to cause a concentration-dependent increase in GCase activity. Moreover, when compared to IFG-tartrate, test compounds, the hydro- Samples were again clarified by centrifugation and 75 µl of the supernatant was combined with 75 µl of acetonitrile. Samples were then analyzed for compound levels by LC-MS/MS at PPD Inc. (3230 Deming Way, Middleton, Wis. 53562).

In brief, a Thermo Betasil, Silica-100, 50×3 mm, 5μ column equilibrated with a mixture of mobile phase consisting of 5 mM ammonium formate and 0.05% formic acid in (A) 95:5 acetonitrile:water or (B) 70:20:10 methanol:water:acetonitrile was employed. Between 20 and 30 μl sample was injected for analysis. Notably, the retention times for IFG, Compound A and Compound B are 4.91, 4.33, and 4.32 minutes, respectively. For MS/MS, the analytes were monitored by MRM with the following ion masses (Q1/Q3, amu): IFG 13C2-15N isotopically-labeled internal standard (151.1/115.1), IFG (148.1/112.1), Compound A (150.1/103.1), Compound B (166.2/130.1). When Compound B was analyzed, Compound A was used as internal standard (150.1/130.1). For calculating drug concentrations, raw data for plasma (ng/mL) and brain (ng/g) was converted to nM using the molecular weight of respective compounds and assuming 1 g of tissue is equivalent to 1 mL volume. Concentration as a function of time was plotted in GraphPad Prism version 4.02.

Figure 1A:
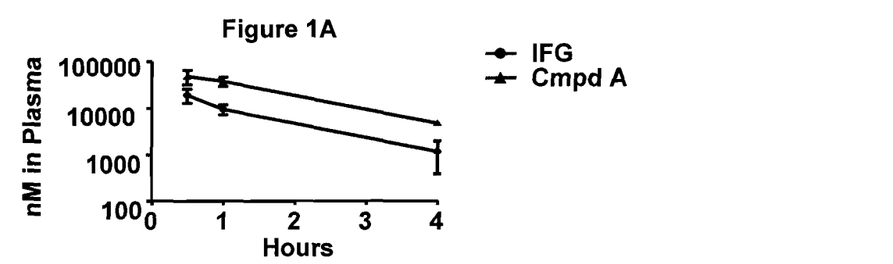
FIG. 1A illustrates the plasma levels of reference compound, IFG, and test compound, (3R,4R,5R)-5-(fluoromethyl)piperidine-3,4-diol (referred to herein as Compound A), in mice administered a single 30 mg/kg (free base equivalent) p.o. dose of IFG-tartrate or the hydrochloride salt form of Compound A.
Figure 1B:
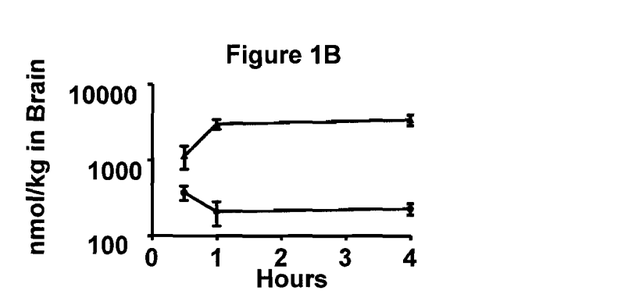
FIG. 1B illustrates the brain levels of reference compound, IFG, and test compound, Compound A, in mice administered a single 30 mg/kg (free base equivalent) p.o. dose of IFG-tartrate or the hydrochloride salt form of Compound A.
Figure 1C:
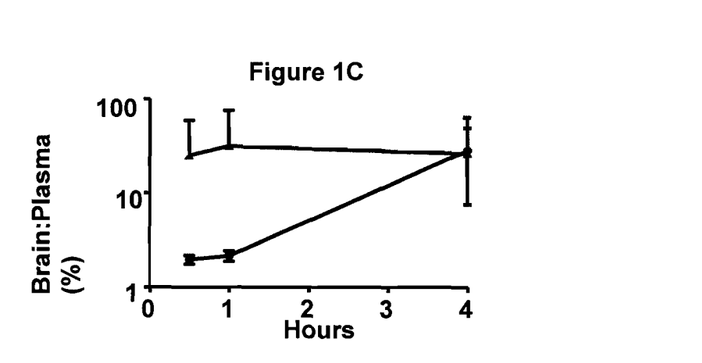
FIG. 1C illustrates the ratio of brain to plasma levels of reference compound, IFG, and test compound, Compound A, in mice administered a single 30 mg/kg (free base equivalent) p.o. dose of IFG-tartrate or the hydrochloride salt form of Compound A.

The plasma levels and brain levels of reference compound, IFG, and test compound, Compound A, detected in mice administered a single 30 mg/kg (free base equivalent) p.o. dose of IFG-tartrate or the hydrochloride salt form of Compound A are illustrated in FIGS. 1A and 1B, respectively. Similarly, the ratio of brain to plasma levels of Compound A and IFG detected in these mice is illustrated in FIG. 1C. Surprisingly, these results reflect that Compound A crossed the blood brain barrier more readily as compared to IFG.

Figure 2:
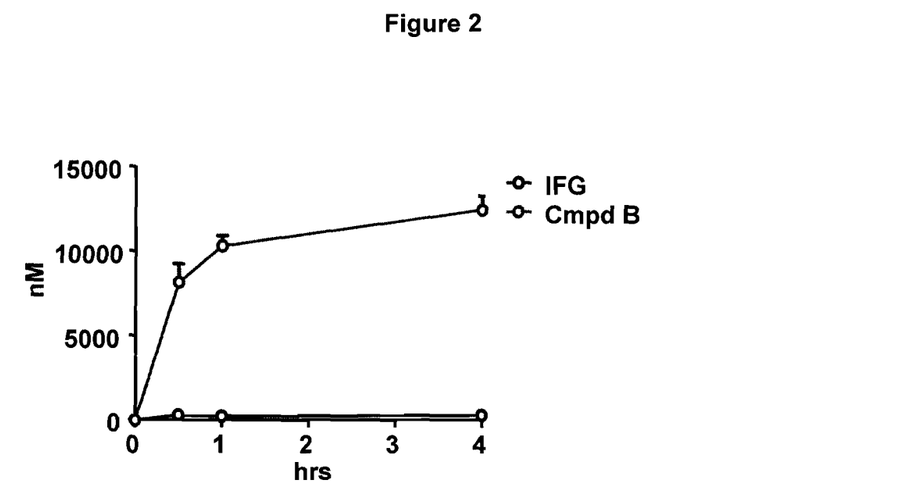
FIG. 2 illustrates the brain levels of reference compound, IFG, and test compound, (3R,4R,5S)-5-(chloromethyl)piperidine-3,4-diol (referred to herein as Compound B), in mice administered a single 30 mg/kg (free base equivalent) p.o. dose of IFG-tartrate or free-base of Compound B.
Figure 3:
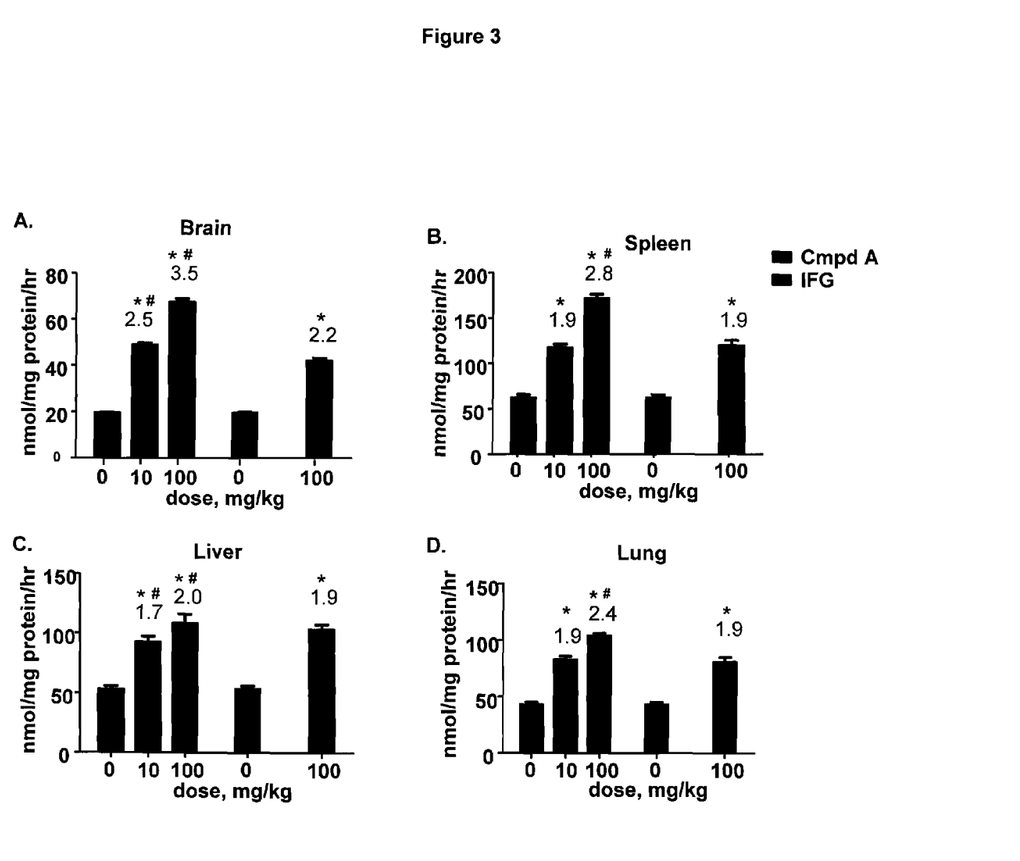
FIGS. 3A-D illustrate the level of GCase in brain, spleen, liver and lung, respectively, of C57BL/6 mice administered a 2-week dosing regimen consisting of nine doses of (i) control vehicle; (ii) 100 mg/kg (free base equivalent) of reference compound, IFG-tartrate; or (iii) 10 or 100 mg/kg (free base equivalent) of test compound, the hydrochloride salt form of Compound A. Note that the values appearing above the bars in these figures represent the fold increase above control. Likewise, in these figures, the symbol "*" represents p<0.05 t-test compared to control and the symbol "#" represents p<0.05 t-test compared to mice treated with reference compound, IFG-tartrate.
Figure 4:
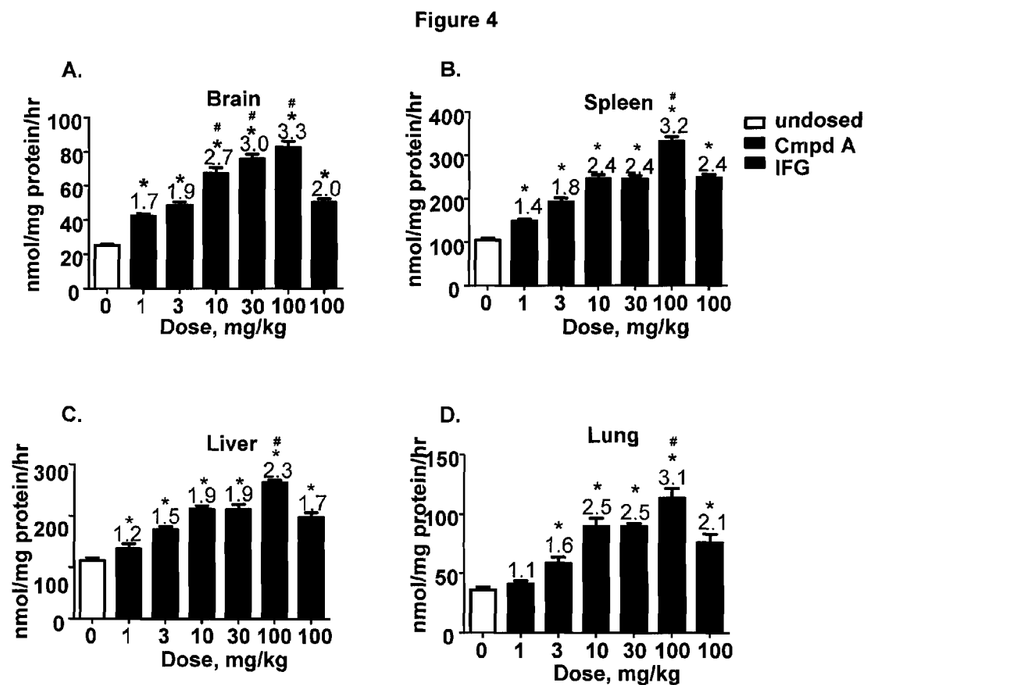
FIGS. 4A-D illustrate the level of GCase in brain, spleen, liver and lung, respectively, of C57BL/6 mice administered a 2-week dosing regimen consisting of nine doses of (i) control vehicle; (ii) 100 mg/kg (free base equivalent) of reference compound, IFG-tartrate; or (ii) 1, 3, 10, 30 or 100 mg/kg (free base equivalent) of test compound, the hydrochloride salt form of Compound A. Note that the values appearing above the bars in these figures represent the fold increase above control. Likewise, in these figures, the symbol "*" represents p<0.05 t-test compared to control and the symbol "#" represents p<0.05 t-test compared to mice treated with reference compound, IFG-tartrate.
Figure 5:
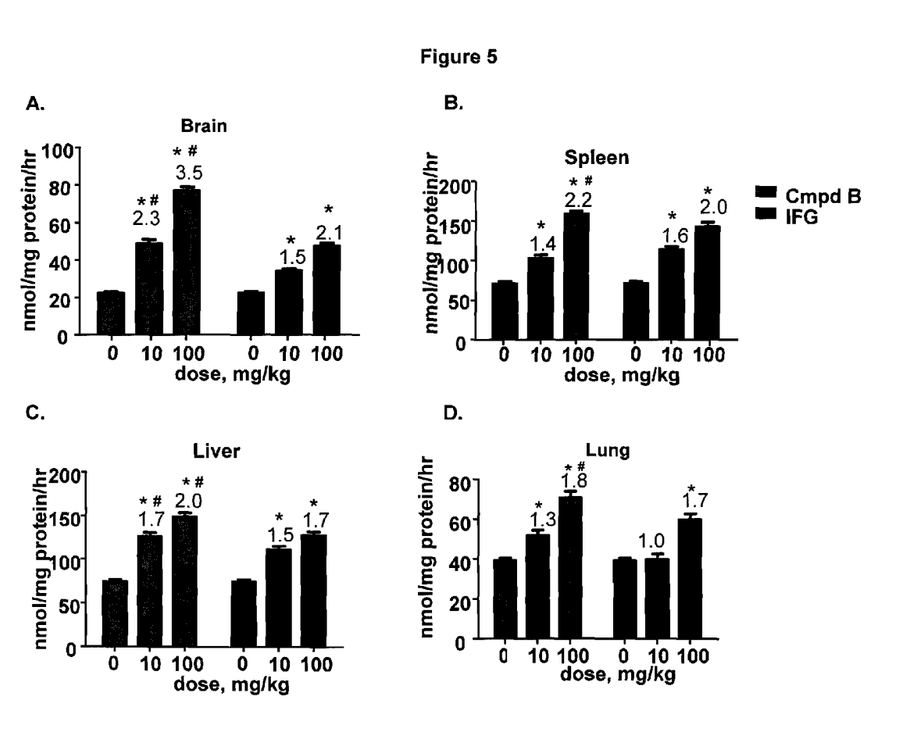
FIGS. 5A-D illustrate the level of GCase in brain, spleen, liver and lung, respectively, of C57BL/6 mice administered a 2-week dosing regimen consisting of nine doses of (i) control vehicle; (ii) 10 or 100 mg/kg (free base equivalent) of reference compound, IFG-tartrate; or (iii) 10 or 100 mg/kg (free base equivalent) of test compound, Compound B. Note that the values appearing above the bars in these figures represent the fold increase above control. Likewise, in these figures, the symbol "*" represents p<0.05 t-test compared to control and the symbol "#" represents p<0.05 t-test compared to mice treated with reference compound, IFG-tartrate.

The brain levels of reference compound, IFG, and test compound, Compound B, detected in mice administered a single 30 mg/kg (free base equivalent) p.o. dose of IFG-tartrate or free base form of Compound B is illustrated in FIG. 2. Notably, even higher levels of Compound B were detected in brain than that observed following administration of the hydrochloride salt form of Compound A.

Example 3

GCase Enhancement

The ability of orally administered test compounds (the hydrochloride salt form of Compound A and Compound B) to elevate GCase levels as compared to reference compound, IFG-tartrate, was assessed in mice. For this purpose, 8-week old wild-type male mice (C57/BL6) were administered a single p.o. (gavage) dose (detailed in FIGS. 3A-D, 4A-D, and 5A-D) of control, reference compound (IFG-tartrate) or test compound (the hydrochloride salt form of Compound A or Compound B). Seven animals were used per dose. The dosing solutions were prepared in water. Compounds were administered over 2 weeks as follows: week 1, Mon-Fri (On), Sat-Sun (Off); week 2, Mon-Thu (On); necropsy on Friday. Thus, a total of 9 doses (dosing solutions prepared fresh every day) were given to each mouse, with a 24-hour washout between the last dose and necropsy.

After completion of dosing, mice were euthanized with $CO_2$ and whole blood was drawn into lithium heparin tubes from the inferior vena cava. Plasma was collected by spinning blood at 2700 g for 10 minutes at 4° C. Liver, spleen, lung, and brain tissues were removed, washed in cold PBS, blotted dry, flash frozen on dry ice, and stored at −80° C. until analysis. GCase levels were measured by homogenizing approximately 50 mg tissue in 500 μL McIlvane (MI) buffer (100 mM sodium citrate, 200 mM sodium phosphate dibasic, 0.25% sodium taurocholate, and 0.1% Triton X-100, pH 5.2) at pH 5.2 for 3-5 seconds on ice with a micro homogenizer. Homogenates were then incubated at room temperature without and with 2.5 mM conduritol-B-epoxide (CBE) for 30 min. Finally, 3.7 mM 4-methylumbeliferryl-β-glucoside (4-MUG) substrate was added and incubated at 37° C. for 60 min. Reactions were stopped by addition of 0.4 M glycine, pH 10.6. Fluorescence was measured on a plate reader for 1 sec/well using 355 nm excitation and 460 nm emission. Total protein was determined in lysates using the MicroBCA kit according to the manufacturer's instructions. A 4-methylumbelliferone (4-MU) standard curve ranging from 1.0 nM to 50 μM was run in parallel for conversion of raw fluorescence data to absolute GCase activity (in the presence and absence of CBE) and expressed as nanomoles of 4-MU released per milligram of protein per hour (nmol/mg protein/hr). GCase levels and protein levels were calculated using Microsoft Excel (Redmond, Wash.) and GraphPad Prism version 4.02.

FIGS. 3A-D illustrate the level of GCase in brain, spleen, liver and lung, respectively, of C57BL/6 mice administered a 2-week dosing regimen consisting of nine doses of (i) control vehicle; (ii) 100 mg/kg (free base equivalent) of reference compound, IFG-tartrate; or (iii) 10 or 100 mg/kg (free base equivalent) of test compound, the hydrochloride salt form of Compound A. Furthermore, Tables 3A-C detail the level of GCase enhancement in brain, spleen, and plasma, respectively, of mice treated as described above.

TABLE 3A

Brain samples of GCase enhancement study

| Compound | Dose (mg/kg) | Dosing solution | GCase increase (-fold) | Concentration (nM) | IC50 pH 5.2 (nM) |
|---|---|---|---|---|---|
| Compound A | 10 | water | 2.5 | 124 ± 11 (0.5) | 10 ± 1 |
| Compound A | 100 | water | 3.5 | 726 ± 51 (3) | |
| IFG | 100 | water | 2.2 | 182 ± 13 (0.7) | 50 ± 3 |

Notes:
BLQ < 5 ng/g
Values in parenthesis indicate concentrations in GCase assays after dilution
IC50 data is average of three independent experiments

TABLE 3B

Spleen samples of GCase enhancement study

| Compound | Dose (mg/kg) | Dosing solution | GCase Increase (-fold) | Concentration (nM) | IC50 pH 5.2 (nM) |
|---|---|---|---|---|---|
| Compound A | 10 | water | 1.9 | 69 ± 6 (0.3) | 10 ± 1 |
| Compound A | 100 | water | 2.8 | 304 ± 63 (1.1) | |
| IFG | 100 | water | 1.9 | 711 ± 100 (2.6) | 50 ± 3 |

Notes:
BLQ < 8 ng/g
Values in parenthesis indicate concentrations in GCase assays after dilution
IC50 data is average of three independent experiments

TABLE 3C

Plasma samples of GCase enhancement study

| Compound | Dose (mg/kg) | Dosing solution | Concentration (nM) |
|---|---|---|---|
| Compound A | 10 | water | 32 ± 2.4 |
| Compound A | 100 | water | 254 ± 73.5 |
| IFG | 100 | water | 330 ± 36 |

Note:
BLQ < 1 ng/mL

Similarly, FIGS. 4A-D illustrate the level of GCase in brain, spleen, liver and lung, respectively, of C57BL/6 mice administered a 2-week dosing regimen consisting of nine doses of (i) control vehicle; (ii) 100 mg/kg (free base equivalent) of reference compound, IFG-tartrate; or (ii) 1, 3, 10, 30 or 100 mg/kg (free base equivalent) of test compound, the hydrochloride salt form of Compound A.

As reflected in FIGS. 3A-D and 4A-D as well as Tables 3A-3C, mice administered the hydrochloride salt form of Compound A demonstrated statistically significant greater GCase enhancement in brain, spleen, liver and lung as compared to mice administered control or IFG-tartrate. Moreover, GCase enhancement in mice administered the hydrochloride salt form of Compound A was unexpectedly greater than that observed with IFG-tartrate even when far lower doses of the hydrochloride salt form of Compound A were administered than IFG-tartrate.

Likewise, FIGS. 5A-D illustrate the level of GCase detected in brain, spleen, liver, and lung, respectively, of mice treated with Compound B and IFG-tartrate as described above. Furthermore, Tables 4A-4C detail the level of GCase enhancement in brain, spleen, and plasma, respectively, of mice treated as described above.

TABLE 4A

Brain samples of GCase enhancement study

| Compound | Dose (mg/kg) | Dosing solution | GCase Increase (-fold) | Concentration (nM) | IC50 pH 5.2 (nM) |
|---|---|---|---|---|---|
| Compound B | 10 | water | 2.3 | 246 ± 42 (0.9) | 73 ± 9 |
| Compound B | 100 | water | 3.5 | 2066 ± 231 (7.6) | |
| IFG | 10 | water | 1.5 | 49 ± 2.4 (0.2) | 50 ± 3 |
| IFG | 100 | water | 2.1 | 287 ± 74 (1.1) | |

Notes:
BLQ < 5 ng/g
Values in parenthesis indicate concentrations in GCase assays after dilution
IC50 data is average of three independent experiments

TABLE 4B

Spleen samples of GCase enhancement study

| Compound | Dose (mg/kg) | Dosing solution | GCase Increase (-fold) | Concentration (nM) | IC50 pH 5.2 (nM) |
|---|---|---|---|---|---|
| Compound B | 10 | water | 1.4 | 645 ± 214 (2.4) | 73 ± 9 |
| Compound B | 100 | water | 2.2 | 2156 ± 464 (8) | |
| IFG | 10 | water | 1.6 | 150 ± 12 (0.5) | 50 ± 3 |
| IFG | 100 | water | 2.0 | 1139 ± 220 (4.2) | |

Notes:
BLQ < 5 ng/g
Values in parenthesis indicate concentrations in GCase assays after dilution
IC50 data is average of three independent experiments

TABLE 4C

Plasma samples of GCase enhancement study

| Compound | Dose (mg/kg) | Dosing solution | Concentration (nM) |
|---|---|---|---|
| Compound B | 10 | water | 104.3 ± 15 |
| Compound B | 100 | water | 1529 ± 601 |
| IFG | 10 | water | 67 ± 10 |
| IFG | 100 | water | 852 ± 134 |

Note:
BLQ < 1 ng/mL

As reflected in FIGS. 5A-D as well as Tables 4A-4C, mice administered Compound B demonstrated statistically significant greater GCase enhancement in brain, spleen, liver and lung as compared to mice administered control or IFG-tartrate. Moreover, GCase enhancement in mice administered Compound B was unexpectedly greater than that observed with IFG-tartrate even when far lower doses of Compound B were administered than IFG-tartrate.

Example 4

Rat Pharmacokinetics

Pharmacokinetic (PK) data was obtained in rats to assess the bioavailability of test compound. In particular, the following PK parameters were calculated: bioavailability as measured by area under the Concentration/Time curve (AUC), fraction of dose available (% F; further defined below), clearance (CL), volume of distribution (Vd), and half-life (t½). For this purpose, 8-week old Sprague-Dawley male rats were given either a single intravenous (IV) dose equivalent to 3 mg/kg of free base or single escalating p.o. (gavage) doses of test compound equivalent to 10, 30, and 100 mg/kg of free base. Three rats were used per dosing group. Blood was collected over a 24-hr period. The time points for blood collection after intravenous administration were: 0, 2.5, 5, 10, 15, 30, 45 min, 1, 2, 4, 8, 12, and 24 hrs; time points for blood collection after p.o. administrations were: 0, 5, 15, 30, 45 min, 1, 2, 3, 4, 8, 12, and 24 hrs. Plasma samples were analyzed for compound levels by LC-MS/MS at PPD. Raw data was analyzed by non-compartmental analysis in Win-nonLin to calculate Vd, % F, CL, and t½.

Figure 6A:
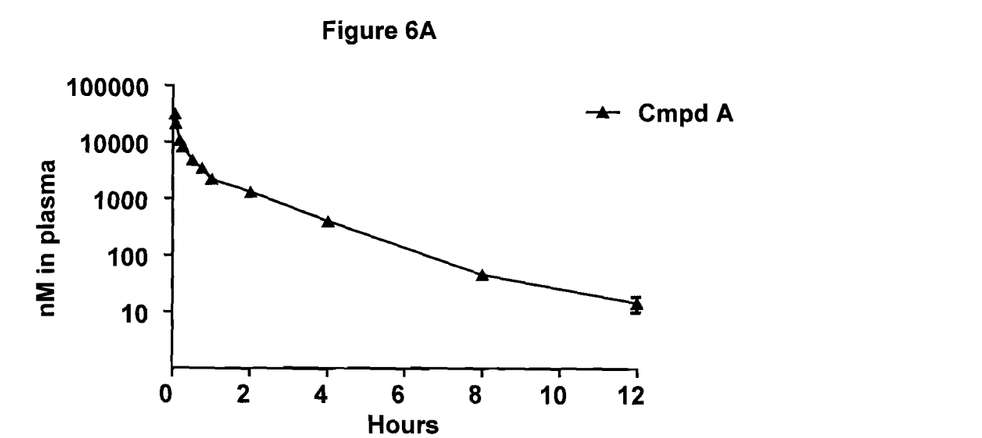
FIG. 6A illustrates the plasma level of test compound, Compound A, in rats administered a single intravenous dose of 3 mg/kg (free base equivalent) of the hydrochloride salt form of Compound A.
Figure 6B:
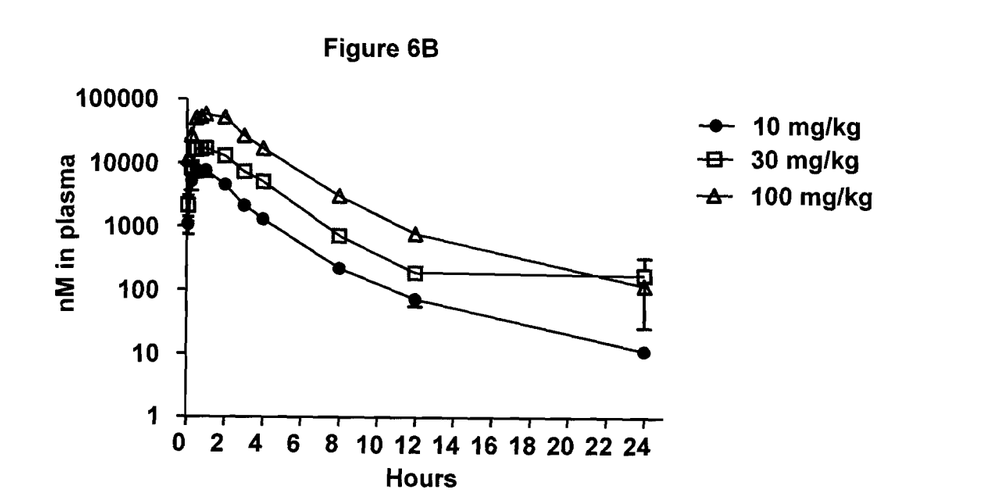
FIG. 6B illustrates the plasma level of Compound A in rats administered a single p.o. dose of 10, 30, or 300 mg/kg (free base equivalent) of the hydrochloride salt form of Compound A.

Plasma levels in rats following a single 3 mg/kg (free base equivalent) intravenous dose of the hydrochloride salt form of Compound A are illustrated in FIG. 6A. Similarly, plasma levels in rats administered a single dose of 10, 30, and 300 mg/kg (free base equivalent) p.o. dose of the hydrochloride salt form of Compound A are illustrated in FIG. 6B. Various pharmacokinetic parameters for Compound A based on the aforementioned study are detailed in Table 5 below.

TABLE 5

Rat PK data for Compound A

| Dose (mg/kg) | | | $AUC_{last}$ | | | Cmax | CL | $V_D$ |
|---|---|---|---|---|---|---|---|---|
| Salt | Free Base | Route | (hr*ng/mL) | % F | t1/2 (h) | (ng/mL) | (mL/hr/kg) | (mL/kg) |
| 3.72 | 3 | IV | 1798 ± 42.7 | N/A | 1.4 ± 0.1 | 7274 ± 139 | 1666 ± 38.5 | 3481 ± 232 |
| 12.4 | 10 | PO | 2982 ± 228 | 50 3.8 | 1.2 ± 0.4 | 1289 ± 271 | 3387 ± 277 | 13283 ± 1929 |
| 37.2 | 30 | PO | 8251 ± 388 | 46 2.5 | 2.3 ± 0.3 | 2870 ± 355 | 4009 ± 509 | 13532 ± 3291 |
| 124 | 100 | PO | 29606 ± 1748 | 49 2.7 | 2.6 ± 0.1 | 9393 ± 742 | 3393 ± 209 | 13101 ± 1518 |

Notes:
Non compartmental analysis mean values (N = 3 rats)
BLD Below Limit of Detection (<0.5 ng/mL)
BLQ Below Limit of Quantitation $$\% \text{ F} = \frac{\text{AUC PO} \times 100 \text{ dose normalized}}{\text{AUC IV}}$$

$AUC_{last}$ = Area under the Concentration/Time curve to the last data point

As reflected in FIGS. 6A and 6B as well as Table 5, the hydrochloride salt form of Compound A has a favorable pharmacokinetic profile for drug development as a pharmacological chaperone. In particular, the hydrochloride salt form of Compound A shows good oral bioavailability (~50%) and dose proportionality, a half-life of 1.0 to 2.5 hours, and a volume of distribution suggesting adequate penetration into peripheral tissues.

What is claimed:

1. A method for treating a lysosomal storage disorder, which comprises administering to a patient diagnosed with at least one condition selected from the group consisting of Gaucher disease, accumulation of glucocerebroside, deficiency in glucocerebrosidase, and a mutation in a glucocerebrosidase enzyme an effective amount of a therapeutic agent selected from the group consisting of 5-(fluoromethyl)piperidine-3,4-diol, 5-(chloromethyl)piperidine-3,4-diol, a pharmaceutically acceptable salt of any of the above, a solvate of any of the above, and any combination of two or more thereof.

2. The method of claim 1, which comprises administering 5-(fluoromethyl)piperidine-3,4-diol or a pharmaceutically acceptable salt thereof or a solvate thereof.

3. The method of claim 1, which comprises administering 5-(chloromethyl)piperidine-3,4-diol or a pharmaceutically acceptable salt thereof or a solvate thereof.

4. The method of claim 1, which comprises administering (3R, 4R, 5S)-5-(chloromethyl)piperidine-3,4-diol or a pharmaceutically acceptable salt thereof or a solvate thereof.

5. The method of claim 1, which comprises administering (3R, 4R, 5S)-5-(chloromethyl)piperidine-3,4-diol.

6. The method of claim 1, wherein the lysosomal storage disorder is associated with accumulation of glucocerebroside.

7. The method of claim 1, wherein the lysosomal storage disorder is associated with a deficiency in glucocerebrosidase.

8. The method of claim 1, wherein the lysosomal storage disorder is associated with a mutation in glucocerebrosidase.

9. The method of claim 1, further comprising administering an effective amount of at least one other therapeutic agent.

10. The method of claim 9, wherein at least one other therapeutic agent is imiglucerase or 1,5-(butylimino)-1,5-dideoxy-D-glucitol.

11. A method for treating Gaucher's disease in a patient diagnosed with the same, which comprises administering to the patient in need thereof an effective amount a therapeutic agent selected from the group consisting of 5-(fluoromethyl)piperidine-3,4-diol, 5-(chloromethyl)piperidine-3,4-diol, a pharmaceutically acceptable salt of any of the above, a solvate of any of the above, and any combination of two or more thereof.

12. The method of claim 11, which comprises administering -(fluoromethyl)piperidine-3,4-diol or a pharmaceutically acceptable salt thereof or a solvate thereof.

13. The method of claim 11, which comprises administering -(fluoromethyl)piperidine-3,4-diol hydrochloride.

14. The method of claim 11, which comprises administering -(chloromethyl)piperidine-3,4-diol or a pharmaceutically acceptable salt thereof or a solvate thereof.

15. The method of claim 11, which comprises administering -(chloromethyl)piperidine-3,4-diol.

16. The method of claim 11, further comprising administering an effective amount of at least one other therapeutic agent.

17. The method of claim 16, wherein at least one other therapeutic agent is imiglucerase or 1,5-(butylimino)-1,5-dideoxy-D-glucitol.

18. A kit comprising a composition comprising an effective amount of 5-(fluoromethyl)piperidine-3,4-diol, 5-(chloromethyl)piperdine-3,4-diol, or a pharmaceutically acceptable salt, solvate, or combination thereof in a container and instructions for using the composition to treat Gaucher's disease.

* * * * *